(12) United States Patent
Riddell

(10) Patent No.: US 6,319,342 B1
(45) Date of Patent: Nov. 20, 2001

(54) METHOD OF FORMING MELTBLOWN WEBS CONTAINING PARTICLES

(75) Inventor: Wilfred Eugene Riddell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/419,039

(22) Filed: Oct. 15, 1999

Related U.S. Application Data

(60) Provisional application No. 60/114,307, filed on Dec. 31, 1998.

(51) Int. Cl.[7] .............................. A61F 13/15; B32B 27/02
(52) U.S. Cl. ..................... 156/62.4; 156/167; 156/181; 264/6; 264/113; 264/121
(58) Field of Search .................................. 156/62.4, 167, 156/181, 276; 264/113, 121, 6–8

(56) References Cited

U.S. PATENT DOCUMENTS

| | | |
|---|---|---|
| 2,345,533 | 3/1944 | Graves . |
| 3,793,678 | 2/1974 | Appel . |
| 3,849,241 | 11/1974 | Butin et al. . |
| 3,862,287 | 1/1975 | Davis . |
| 3,881,490 | 5/1975 | Whitehead et al. . |
| 3,971,373 | 7/1976 | Braun . |
| 4,100,324 | 7/1978 | Anderson et al. . |
| 4,116,738 | 9/1978 | Pall . |
| 4,307,143 | 12/1981 | Meitner . |
| 4,340,563 | 7/1982 | Appel et al. . |
| 4,372,312 | 2/1983 | Fendler et al. . |
| 4,429,001 | 1/1984 | Kolpin et al. . |
| 4,560,372 | 12/1985 | Pieniak . |
| 4,604,313 | 8/1986 | McFarland et al. . |
| 4,655,757 | 4/1987 | McFarland et al. . |
| 4,659,609 | 4/1987 | Lamers et al. . |
| 4,675,209 | 6/1987 | Pedigrew . |
| 4,707,398 | 11/1987 | Boggs . |

(List continued on next page.)

FOREIGN PATENT DOCUMENTS

| | | |
|---|---|---|
| 0 080 382 A2 | 6/1983 | (EP) . |
| 0 156 160 A2 | 10/1985 | (EP) . |
| 0 174 775 A1 | 3/1986 | (EP) . |
| 0 305 620 B1 | 7/1993 | (EP) . |
| 0 571 981 A1 | 12/1993 | (EP) . |
| 0 333 228 B1 | 2/1994 | (EP) . |
| 0 333 212 B1 | 11/1994 | (EP) . |
| 0 622 064 A2 | 11/1994 | (EP) . |
| 0 625 602 A1 | 11/1994 | (EP) . |
| 0 729 735 A1 | 9/1996 | (EP) . |
| 0 479 442 B1 | 6/1997 | (EP) . |
| 0 710 096 B1 | 8/1997 | (EP) . |
| 0 720 488 B1 | 3/1999 | (EP) . |
| 2764185 | * 12/1998 | (FR) . |
| WO 93/06804 A1 | 4/1993 | (WO) . |
| WO 95/03019 A1 | 2/1995 | (WO) . |

(List continued on next page.)

Primary Examiner—Sam Chuan Yao
(74) Attorney, Agent, or Firm—Thomas M. Parker

(57) ABSTRACT

A method of forming a meltblown web having meltblown fibers and particles is provided. The particles are heated to a temperature approximating that of the meltblown fibers as they are being extruded. As a portion of any heated particle impacts the skin of one or more solidifying meltblown fibers, that portion of any heated particle penetrates into one or more solidifying particles. Although a portion of any particle becomes embedded in and retained by one or more meltblown fibers, such surface penetration is generally slight desirably leaving a substantial amount of surface area of any particle available for interaction with any medium to which a web may be exposed.

15 Claims, 13 Drawing Sheets

U.S. PATENT DOCUMENTS

| | | |
|---|---|---|
| 4,724,114 | 2/1988 | McFarland et al. . |
| 4,735,624 | 4/1988 | Mazars . |
| 4,754,773 | 7/1988 | Rex . |
| 4,760,764 | 8/1988 | De Jonckheere et al. . |
| 4,770,344 | 9/1988 | Kaiser . |
| 4,784,892 | 11/1988 | Storey et al. . |
| 4,786,550 | 11/1988 | McFarland et al. . |
| 4,795,482 | 1/1989 | Gioffre et al. . |
| 4,797,318 | 1/1989 | Brooker et al. . |
| 4,800,102 | 1/1989 | Takada . |
| 4,801,494 | 1/1989 | Datta et al. . |
| 4,826,497 | 5/1989 | Marcus et al. . |
| 4,840,692 | 6/1989 | Kamstrup-Larsen . |
| 4,861,405 | 8/1989 | Kassai . |
| 4,882,204 | 11/1989 | Tenenbaum . |
| 4,927,346 | 5/1990 | Kaiser et al. . |
| 4,927,582 | 5/1990 | Bryson . |
| 4,948,639 | 8/1990 | Brooker et al. . |
| 5,028,224 | 7/1991 | Pieper et al. . |
| 5,080,741 | 1/1992 | Nomura et al. . |
| 5,120,693 | 6/1992 | Connolly et al. . |
| 5,123,949 * | 6/1992 | Thiessen ................................ 65/4.4 |
| 5,204,173 | 4/1993 | Canary . |
| 5,206,085 | 4/1993 | Nakagawa et al. . |
| 5,213,817 | 5/1993 | Pelley . |
| 5,350,624 | 9/1994 | Georger et al. . |
| 5,397,316 | 3/1995 | LaVon et al. . |
| 5,417,789 | 5/1995 | Lauritzen . |
| 5,429,630 | 7/1995 | Beal et al. . |
| 5,437,653 | 8/1995 | Gilman et al. . |
| 5,514,104 | 5/1996 | Cole et al. . |
| 5,562,793 | 10/1996 | Menard . |
| 5,614,132 * | 3/1997 | Bakhshi et al. .......................... 264/6 |
| 5,674,339 * | 10/1997 | Groeger et al. ...................... 156/145 |
| 5,713,881 | 2/1998 | Rezai et al. . |
| 5,720,832 | 2/1998 | Minto et al. . |
| 5,770,531 | 6/1998 | Sudduth et al. . |
| 5,843,267 | 12/1998 | Cashaw et al. . |
| 5,876,529 * | 3/1999 | Grant et al. ......................... 156/62.4 |
| 5,922,163 * | 7/1999 | Helynranta et al. ................. 156/296 |

FOREIGN PATENT DOCUMENTS

| | | |
|---|---|---|
| WO 98/24620 A1 | 6/1998 | (WO) . |
| WO 98/28128 A1 | 7/1998 | (WO) . |
| WO 98/48752 A1 | 11/1998 | (WO) . |

* cited by examiner

METHOD OF FORMING MELTBLOWN WEBS CONTAINING PARTICLES

This application claims priority from U.S. Provisional Application No. 60/114,307 filed on Dec. 31, 1998.

BACKGROUND OF THE INVENTION

This invention relates to methods of forming meltblown webs and in particular to methods of forming meltblown webs containing meltblown fibers and particulate material.

It has been desired to provide a method of forming particle-containing meltblown webs for a variety of purposes, wherein a predetermined amount of particles is held in the web while minimizing the amount of "dusting" (i.e., particles undesirably dropping out of the web) the web may suffer.

Various approaches to retaining particles within a web have been proposed. One such approach discloses a self-supporting durable flexible conformable low-pressuredrop porous sheet product that contains a uniform three-dimensional arrangement of discrete particles. The sheet product includes, in addition to the particles, a web of meltblown fibers in which the particles are uniformly dispersed. The particles are physically held, such as by mechanical entanglement, in the web even though there is only point contact between the meltblown fibers and the particles. ("Point contact" occurs when preformed bodies abut one another. It is distinguished from "area contact," such as results when a liquid material is deposited against a substrate, flows over the substrate, and then hardens in place.) Even though the particles are mechanically entangled within the interstices of the web, a portion of the particles still undesirably drop out of the web during handling.

Another approach discloses using adhesive polymers for forming the meltblown web. In addition to being physically entrapped in the web, the particles of this approach are also adhered to the surfaces of the meltblown fibers. Even though this may be viewed as an improvement over retaining particles within a web by point contact, this approach accomplishes its objective with the use of expensive adhesive polymers.

For the foregoing reasons, there is a need for an improved method of forming meltblown webs having particles substantially uniformly and homogeneously dispersed therethrough and retained therein by more than mere point contact or mechanical entanglement, wherein dusting is substantially eliminated without the addition of expensive adhesive polymers.

SUMMARY OF THE INVENTION

The present invention is directed to an improved method of forming meltblown webs having particles substantially uniformly and homogeneously dispersed therethrough that satisfies the need to substantially eliminate dusting without the addition of expensive adhesive polymers.

One embodiment of the present invention provides for a method of forming a meltblown web having at least one layer, the method including forming a first primary stream containing meltblown fibers. A first secondary stream is formed containing staple fibers and merged with the first primary stream so that the first primary stream includes the staple fibers entangled with the meltblown fibers. Thereafter, the first primary stream including the staple fibers entangled with the meltblown fibers is directed onto a moving forming surface to form a first layer having the staple fibers entangled with the meltblown fibers. After the first layer is formed, this embodiment of the invention provides for forming at least one particle-containing layer by forming a second primary stream having meltblown fibers. A first tertiary stream is formed containing particles and merged with the second primary stream so that the second primary stream contains particle-containing meltblown fibers. A second secondary stream is formed containing staple fibers and merged with the second primary stream so that the second primary stream includes the staple fibers entangled with the particle-containing meltblown fibers. Thereafter, the second primary stream including the staple fibers entangled with the particle-containing meltblown fibers is directed onto the first layer on the moving forming surface to form a second layer having the staple fibers entangled with the particle-containing meltblown fibers.

An alternative embodiment of the present invention provides for the formation of a meltblown web having at least one layer, the method including forming a primary stream of meltblown fibers. A tertiary stream containing particles is formed and merged with the primary stream so that the primary stream includes particle-containing meltblown fibers. Thereafter, the primary stream having particle-containing meltblown fibers is directed onto a moving forming surface to form a layer including the particle-containing meltblown fibers.

Still another embodiment of the present invention provides for forming a meltblown web having at least one layer, the method including forming a primary stream containing meltblown fibers. A tertiary stream containing particles is formed and merged with the primary stream so that the primary stream includes particle-containing meltblown fibers. A secondary stream having staple fibers is formed and merged with the primary stream so that the primary stream includes staple fibers entangled with the particle-containing meltblown fibers. Thereafter, the primary stream having the staple fibers entangled with the particle-containing meltblown fibers is directed onto a moving forming surface to form a layer having the staple fibers entangled with the particle-containing meltblown fibers.

DRAWINGS

The foregoing and other features, aspects and advantages of the present invention will become better understood with regard to the following description, appended claims and accompanying drawings where:

DESCRIPTION OF THE INVENTION

The meltblown webs formed according to the methods of the present invention generally include at least one layer having meltblown fibers and particles.

As used herein, the term "meltblown fibers" means fibers formed by extruding a molten thermoplastic material through a plurality of fine, usually circular, die capillaries as molten threads or filaments into a high velocity stream of heated gas, usually air, which attenuates the filaments of molten thermoplastic material to reduce their diameter. Thereafter, the meltblown fibers are carried by the high velocity gas stream and deposited on a collecting surface to form a web of randomly disbursed meltblown fibers. Meltblowing is generally described, for example, in U.S. Pat. No. 3,849,241 to Buntin, U.S. Pat. No. 4,307,143 to Meitner, et al., and U.S. Pat. No. 4,707,398 to Wisneski et al., each of which is incorporated herein by reference.

Figure 11:
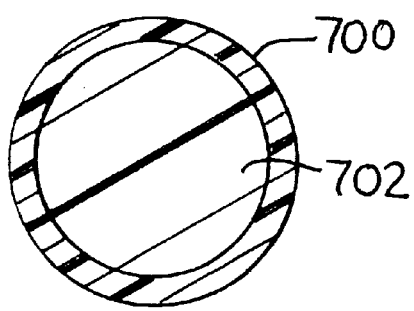
FIG. 11 illustrates an enlarged cross-sectional view of a solidifying thermoplastic polymeric meltblown fiber.
Figure 12:
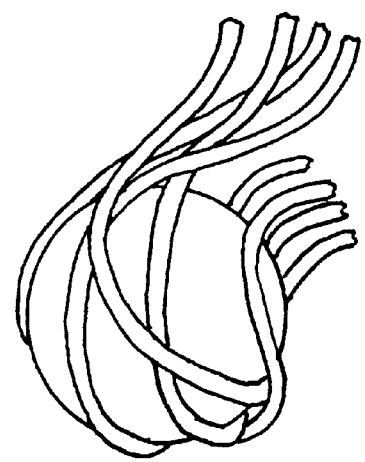
FIG. 12 illustrates an enlarged view of a particle retained within a web of the present invention by surface penetration into more than one meltblown fiber.
Figure 13:
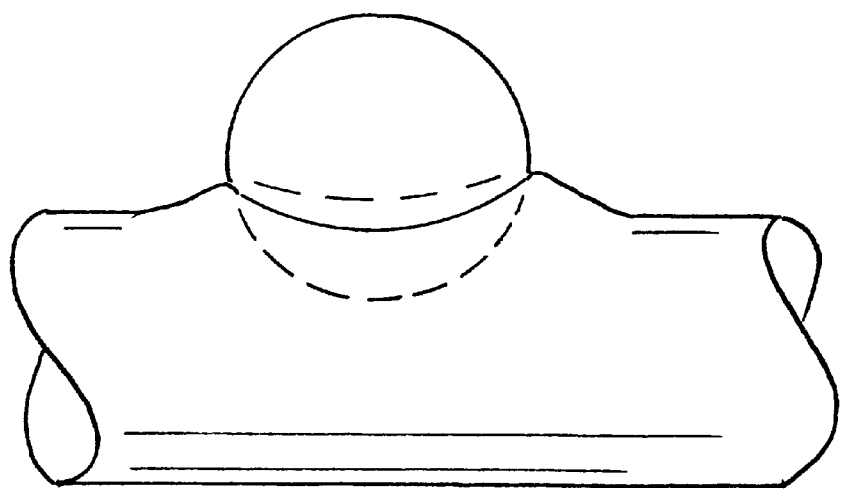
FIG. 13 illustrates an enlarged view of a particle retained within a web of the present invention by surface penetration into at least one meltblown fiber.
Figure 14:
FIG. 14 is a scanning electron microscope photograph, at a magnification level of 10×, illustrating an example of the surface penetration of a particle, having a diameter of about 20 to about 300 microns, into one or more meltblown fibers of a coform web of the present invention.
Figure 15:
FIG. 15 is a scanning electron microscope photograph, at a magnification level of 10×, illustrating an example of the surface penetration of a particle, having a diameter of about 20 to about 300 microns, into one or more meltblown fibers of a coform web of the present invention.
Figure 16:
FIG. 16 is a scanning electron microscope photograph, at a magnification level of 10×, illustrating an example of the surface penetration of a particle, having a diameter of about 20 to about 300 microns, into one or more meltblown fibers of a coform web of the present invention.
Figure 17:
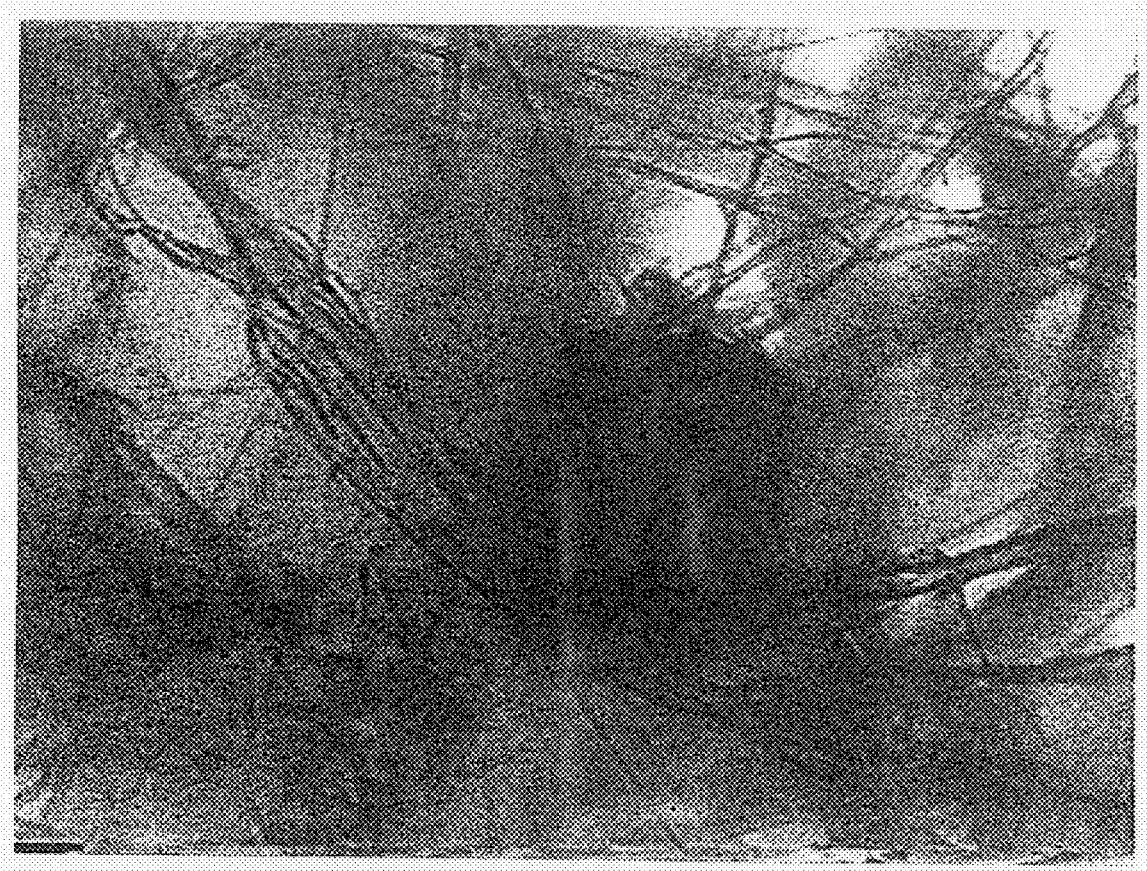
FIG. 17 is a scanning electron microscope photograph, at a magnification level of 10×, illustrating an example of the surface penetration of a particle, having a diameter of about 20 to about 300 microns, into one or more meltblown fibers of a coform web of the present invention.
Figure 18:
FIG. 18 is a scanning electron microscope photograph, at a magnification level of 10×, illustrating an example of the surface penetration of a particle, having a diameter of about 20 to about 300 microns, into one or more meltblown fibers of a coform web of the present invention.
Figure 19:
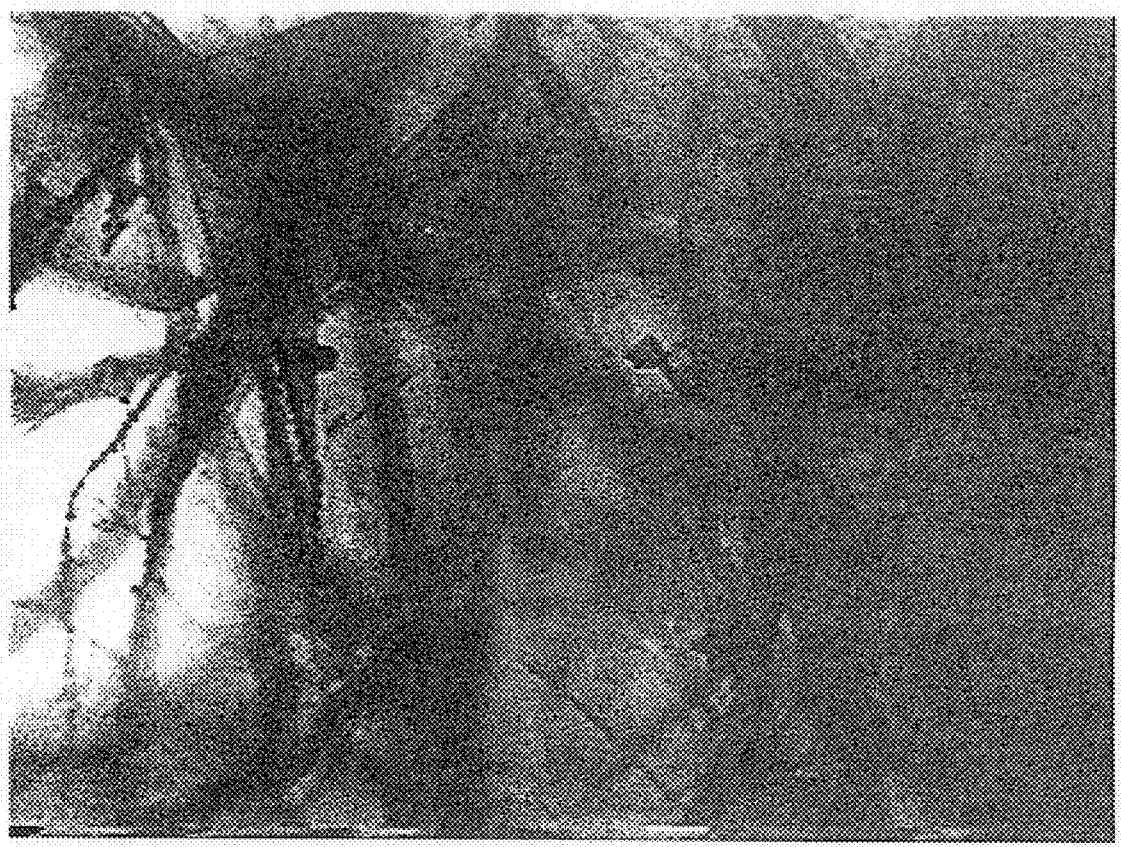
FIG. 19 is a scanning electron microscope photograph, at a magnification level of 10×, illustrating an example of the surface penetration of a particle, having a diameter of about 5 to about 25 microns, into one or more meltblown fibers of a coform web of the present invention.

In a typical meltblowing process, an extruded filament or fiber generally begins the process of cooling or quenching upon exiting from a forming die. As the individual meltblown fiber cools, it thus begins solidifying. The solidification process typically begins at the exterior of the meltblown fiber and moves toward the center of the meltblown fiber. As the meltblown fiber cools, it develops a surface or skin 700, as illustrated in FIG. 11. Although a skin may be present, there usually remains a molten or semi-molten inner core 702 until the core of the meltblown fiber cools and reaches its solidification temperature. Known methods of incorporating particulate material into a meltblown web provide for the introduction of particulate material at about room temperature into a stream of meltblown fibers. Absent adhesive polymers, this room temperature particulate material is maintained in any resulting meltblown web by either point contact or mechanical entanglement with the meltblown fibers. While both point contact and mechanical entanglement are somewhat effective at maintaining a portion of the particulate material in the web, there remains a portion of the particulate material that is neither in sufficient point contact with the meltblown fibers nor sufficiently mechanically entangled in the meltblown fibers and thus either remains fugitive or easily becomes fugitive upon handling of the web. As a result of a portion of the particulate material remaining fugitive or easily becoming fugitive, these webs suffer from the problem of dusting. Alternatively, where adhesive polymers are used, the particulate material added at room temperature is maintained in any web by adhering to the surface of the meltblown fibers. Although the use of adhesive polymers substantially reduces dusting, adhesive polymers are relatively expensive when compared to nonadhesive-containing polymers.

Unlike situations where the particulate material is maintained within a meltblown web by point contact or mechanical entanglement, the present invention provides for an improved and heretofore unknown method of retaining particles in meltblown webs which substantially eliminates dusting without the use of expensive adhesive polymers. This novel invention provides for using any heat-stable particle that can withstand the force of impact with the skin of one or more meltblown fibers and yet substantially maintain its particle integrity. (The term "heat-stable", as used herein, generally refers to any particle whose physical, chemical or other properties remain unchanged as a result of heat encountered by the particle.) While not desiring to be bound by any particular theory, it is believed that by heating the particles to a temperature approximating that of the fibers being extruded from a forming die, a portion of each particle generally impacts and penetrates into the skin of one or more meltblown fibers. As it thus penetrates into one or more solidifying meltblown fibers, that portion of the heated particle becomes embedded in and retained by one or more solidifying meltblown fibers. Although a portion of the particle becomes embedded in and retained by one or more meltblown fibers, such "surface penetration" of the particle into one or more meltblown fibers is generally slight desirably leaving a substantial amount of the surface area of the particle available for interaction with any medium to which a web of this invention may be exposed. FIGS. 12 through 19 illustrate examples of the surface penetration of a variety of one or more particles into one or more meltblown fibers.

Figure 1:
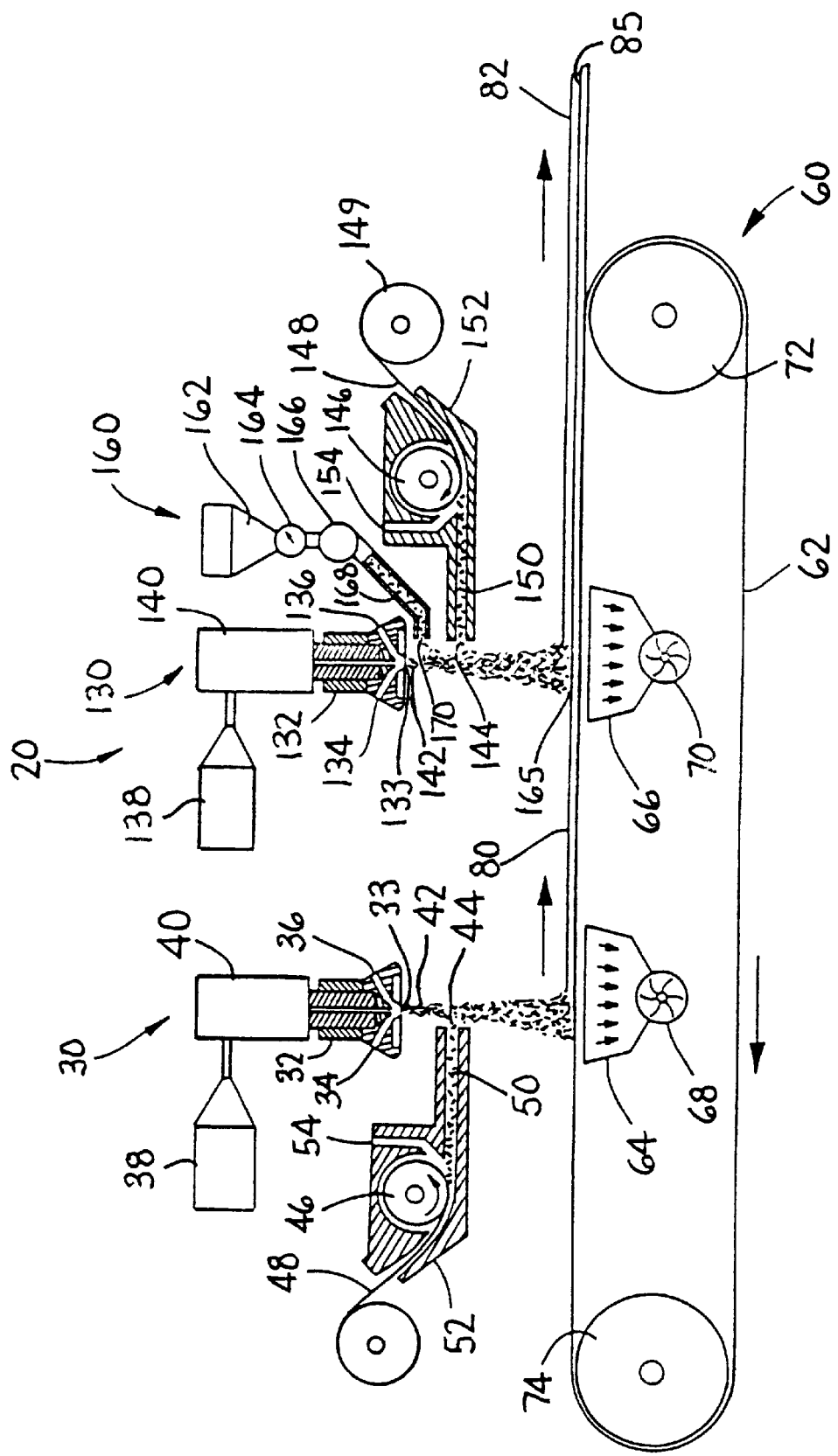
FIG. 1 illustrates a forming apparatus having two units for formation of meltblown fibers with the downstream unit additionally having provision for application of particles.

Referring now to FIG. 1, a forming apparatus, generally indicated as 20, is illustrated as including two meltblown units, 30 and 130, and a movable foraminous belt apparatus, generally indicated as 60. The first meltblown unit 30 includes a forming die 32 having a die tip 33 and a pair of ducts 34 and 36. A material supply and delivery device 38 delivers polymer to extruder 40 for delivery to the forming die 32. A first primary stream 42 including meltblown fibers is formed by a known meltblowing technique, such as is described in U.S. Pat. No. 4,100,324, issued Jul. 11, 1978, to Anderson et al., which is incorporated herein by reference. Basically, the method of formation involves extruding a molten polymeric material through the forming die 32 into streams of polymer and attenuating the polymer streams by converging flows of heated gas, usually air, supplied through ducts 34 and 36.

A first secondary stream 44 including individualized wood or other staple fibers is formed and merged into the first primary stream 42 including meltblown fibers so as to entangle the individualized wood fibers with the meltblown fibers in a single step. The individualized wood fibers typically have a length of about 0.5 to about 10 millimeters and a length to maximum width ratio of about 10:1 to about 400:1. A typical cross-section of an individualized wood fiber has an irregular width of about 10 microns and a thickness of about 5 microns. In the illustrated forming apparatus, the first secondary stream 44 is formed by a pulp sheet divellicating apparatus 52 of the first meltblown unit 30. (The pulp sheet divellicating apparatuses described herein are of the type described in U.S. Pat. No. 3,793,678, issued Feb. 26, 1974, to Appel, which is incorporated herein by reference.) The divellicating apparatus 52 includes a conventional picker roll 46 having picking teeth for divellicating wood pulp sheets 48 into individualized wood fibers. The wood pulp sheets 48 are fed radially along a picker roll radius to the picker roll 46. It is the teeth of the picker roll 46 that divellicate the wood pulp sheets 48 into individualized wood fibers. The resulting individualized wood fibers are conveyed toward the first primary stream 42 through a forming duct 50. A passageway 54 provides process gas, usually air, to the picker roll 46 in sufficient quantity to serve as a medium for conveying the individualized wood fibers through the forming duct 50 at a velocity approaching that of the picker teeth. The process gas may be supplied by conventional means such as a blower, not shown. It has been found that in order to avoid significant fiber clumping or agglomeration, generally referred to as fiber floccing, the individualized wood fibers should be conveyed through the forming duct 50 at substantially the same velocity at which they leave the picker teeth after separation from the wood pulp sheets 48. The apparatus described for formation of a web of meltblown fibers having wood fibers entangled therein, such web now referred to as coform, is known and is more fully described in the previously referenced U.S. Pat. No. 4,100,324, issued Jul. 11, 1978, to Anderson et al. The first primary stream 42, including wood fibers entangled therein from the first secondary stream 44, is then directed onto a moving forming surface 62 that passes beneath the forming die 32. The moving forming surface 62 is provided with suction devices 64 and 66 driven by blowers 68 and 70 that withdraw gas from beneath the moving forming surface 62 and provide for uniform laydown of the entangled meltblown fibers and wood fibers onto the moving forming surface. The moving forming surface 62 is desirably a permeable belt. In addition to being supported by a first roll 72, the moving forming surface 62 is also supported by a second roll 74. While illustrated with two suction devices, the number and size of the suction devices below the moving forming surface may be varied in any suitable manner well known in the art. Further, the movable foraminous belt apparatus 60 may be provided with dust collector devices, not shown, to prevent the escape of any particles and fibers to the atmosphere.

As illustrated in FIG. 1, a first meltblown unit 30 lays down a layer of meltblown fibers having wood or other staple fibers entangled therein as a first layer 80. This first layer 80 passes beneath a second meltblown unit 130 where a second layer 82 is placed thereon and joined to the first layer 80. The second layer 82 is formed by the second meltblown unit 130. The second meltblown unit includes an extruder 140 fed by a material supply and delivery device 138. The extruder 140 feeds to a forming die 132, that is generally similar to the forming die 32 of the first meltblown unit 30, in that the forming die 132 of the second meltblown unit 130 has a die tip 133 and a pair of ducts 134 and 136 through which streams of heated gas, usually air, are supplied to a second primary stream 142. As the gas streams from the ducts 134 and 136 merge and entrain the extruded fibers in the second primary stream 142, the extruded fibers are meltblown into meltblown fibers. The second meltblown unit 130, however, differs from that of the first meltblown unit 30 in that there additionally is provided a source of particles generally indicated as a particle supply unit 160 including a storage hopper 162, having a feed device 164 leading to a source of high velocity heated gas 166, usually air, and a feeder duct 168 providing a first tertiary stream 170 of heated particles to merge with the second primary stream 142. Upon merging with the second primary stream 142, portions of the heated particles from the first tertiary stream impact and penetrate into the skin of one or more solidifying meltblown fibers and become embedded in and retained by one or more meltblown fibers. The resulting particlecontaining meltblown fibers are subsequently entangled with individualized wood fibers supplied by a second secondary stream 144 exiting through a forming duct 150 from a divellicating apparatus 152 of the second meltblown unit 130 and merging with the second primary stream 142. In the divellicating apparatus 152, the picker roll 146 rotates and divellicates the wood pulp sheets 148 as they are unrolled from a pulp supply roll 149. The wood pulp sheets are divellicated and passed through the forming duct 150 and merged with the second primary stream 142. Process gas, usually air, is supplied through a passageway 154 of the divellicating apparatus 152. The second primary stream 142, now having the wood fibers entangled with the particle-containing meltblown fibers, is then directed as a second layer 82 onto the first layer 80 at a laydown point 165. A suction device 66 aids in laydown. Some of the meltblown fibers and wood fibers of the second layer 82, when laid down, become somewhat intermingled with meltblown fibers and wood fibers of the first layer 80 along a formation line 85. This intermingling is such that an integrated coherent two-layered web is formed suitable for processing and use purposes. However, should the first layer 80 and the second layer 82 be pulled apart, they will generally separate on the formation line 85. After leaving the first roll 72, the two-layered web may be further processed by known means such as cutters and stackers, not shown. Moving forming surface 62, in addition to being supported by the first roll 72, is also supported by the second roll 74.

Figure 2:
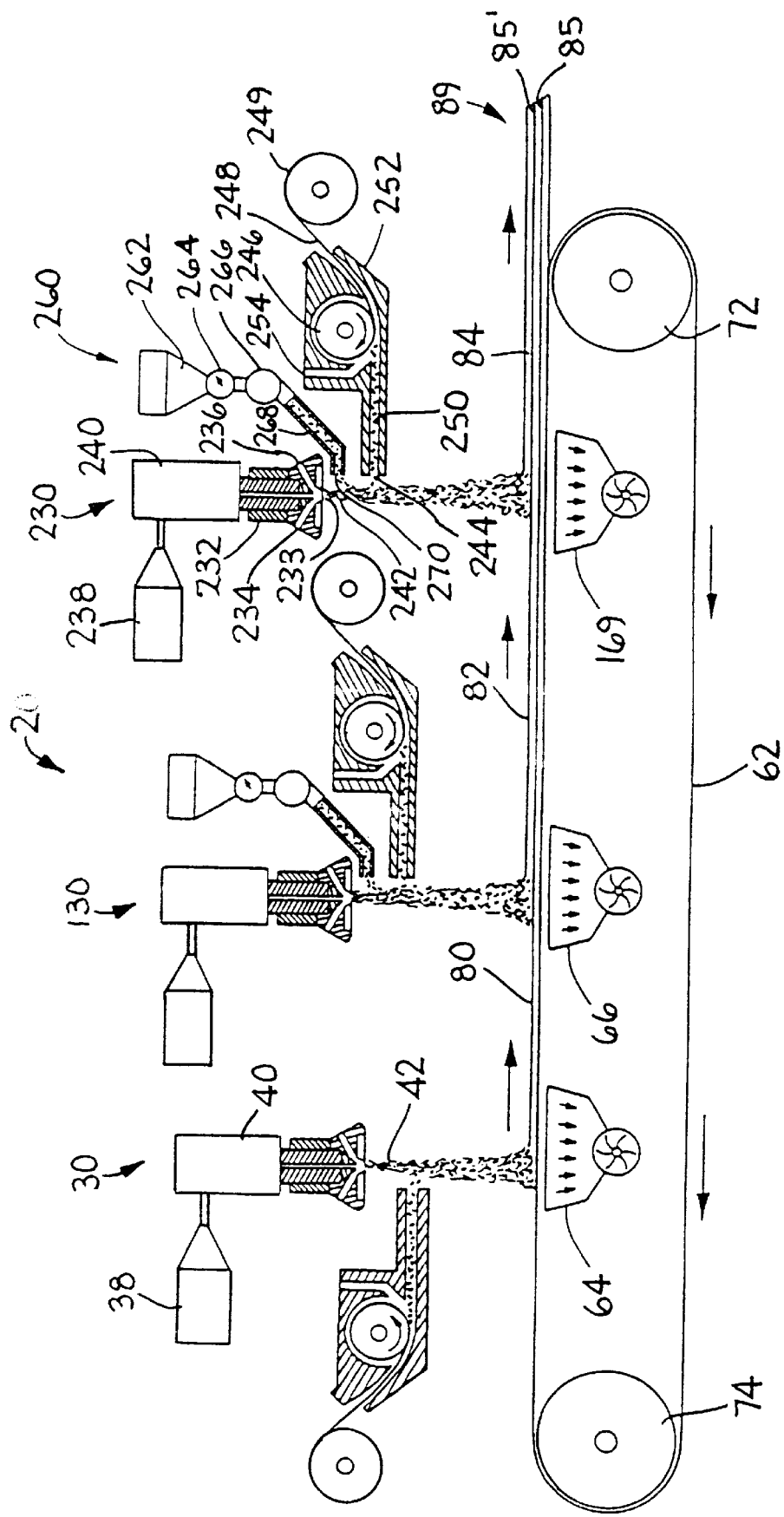
FIG. 2 illustrates a forming apparatus having three units for formation of meltblown fibers with the two downstream units additionally having provision for application of particles.

The apparatus of FIG. 2 is a modified embodiment of the apparatus of FIG. 1 in which the first meltblown unit 30 and the second meltblown unit 130 are placed above a moving forming surface 62. Below the moving forming surface are located at least 3 suction devices 64, 66 and 169. In addition to the first and second meltblown units, there is now a third meltblown unit 230. This third meltblown unit 230 also includes, as the first and second meltblown units do, an extruder 240 fed by a material supply and delivery device 238, leading to a forming die 232. The forming die 232 has therein a die tip 233 and a pair of ducts 234 and 236 through which streams of heated gas, usually air, are supplied to a third primary stream 242. As the gas streams from the ducts 234 and 236 merge and entrain the extruded fibers in the third primary stream 242, the extruded fibers are meltblown into meltblown fibers. Like the second meltblown unit 130, the third meltblown unit 230 differs from that of the first meltblown unit 30 in that there additionally is provided a source of particles generally indicated as a particle supply unit 260 including a storage hopper 262, having a feed device 264 leading to a source of high velocity heated gas 266, usually air, and a feeder duct 268 providing a second tertiary stream 270 of heated particles to merge with the third primary stream 242. Upon merging the second tertiary stream 270 with the third primary stream 242, portions of the heated particles impact and penetrate into the skin of one or more solidifying meltblown fibers and become embedded in and retained by one or more meltblown fibers. The resulting particle-containing meltblown fibers are subsequently entangled with individualized wood fibers supplied by a third secondary stream 244 exiting through a forming duct 250 from a divellicating apparatus 252 of the third meltblown unit 230 and merging with the third primary stream 242. In the divellicating apparatus 252, the picker roll 246 rotates and divellicates the wood pulp sheets 248 as they are unrolled from a pulp supply roll 249. The pulp sheets are divellicated and passed through the forming duct 250 and merged with the third primary stream 242. Process gas, usually air, is supplied through a passageway 254 of the divellicating apparatus 252. In FIG. 2, a first layer 80 is laid down by the first meltblown unit 30. A second layer 82, containing particles, is sourced from the second meltblown unit 130, and a third layer 84, that is sourced from the third meltblown unit 230, are laid down. Some of the meltblown fibers and wood fibers of the second layer 82, when laid down, become somewhat intermingled with the meltblown fibers and wood fibers of the first layer 80 along a formation line 85. Some of the meltblown fibers and wood fibers of the third layer 84, when laid down, become somewhat intermingled with the meltblown fibers and wood fibers of the second layer 82 along a formation line 85'. This intermingling is such that an integrated coherent three-layered web 89 is formed suitable for processing and use purposes. However, should the first layer 80 and the second layer 82 be pulled apart, they will generally separate on the formation line 85. Similarly, should the second layer 82 and the third layer 84 be pulled apart, they will generally separate on the formation line 85'. After leaving the forming apparatus 20, the coherent integrated three-layered web 89 may be treated by conventional means such as cutters and stackers to prepare it for use in an absorbent article. Consequently, the forming apparatus as illustrated in FIG. 2 is capable of forming meltblown webs with particles in either or both of the second and third layers or with only the second layer containing particles if the particle supply unit 260 is not operated.

Because the meltblown fibers are typically much longer, thinner, limper and more flexible than the wood fibers, the meltblown fibers twist around and entangle the relatively short, thick and stiff wood fibers as soon as the two fiber streams merge. This entanglement interconnects the two different types of fibers with strong, persistent inter-fiber attachments without any significant molecular, adhesive or hydrogen bonds. In the resulting matrix, the meltblown fibers retain a high degree of flexibility, with many of the meltblown fibers being spaced apart by engagement with the comparatively stiff wood fibers. The entangled wood fibers are free to change their orientation when the matrix is subjected to various types of distorting forces, but the elasticity and resiliency of the meltblown fiber network tends to return the wood fibers to their original positions when the distorting forces are removed. A coherent integrated web is formed substantially by the mechanical entanglement and intermingling of the two different fibers.

This invention has been described with the formation of a two- or three-layered web. However, it is also within the invention to form coform webs having only a single layer as well as coform webs having more than three layers. For example, the forming apparatus as illustrated in FIG. 1 is capable of forming single-layer coform webs including particles if the first meltblown unit 30 is not operated. Consequently, it is also within the present invention that webs could have a single layer containing particles, or include multiple layers having one or more layers containing particles in a variety of multi-layered configurations.

Figure 3:
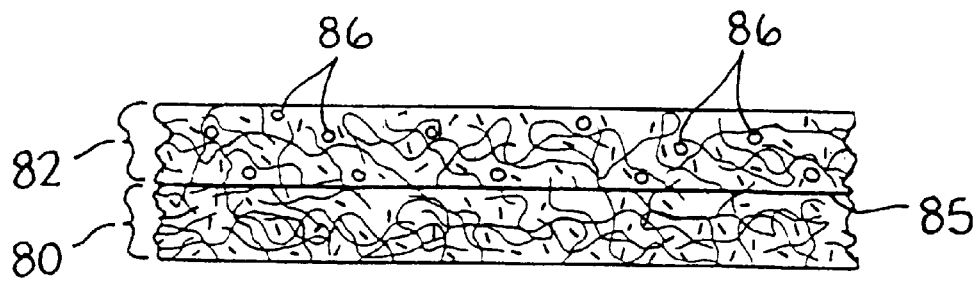
FIG. 3 illustrates a cross-section of a coherent integrated two-layered web of the present invention in which one layer of the web includes particles.

FIG. 3 is illustrative of a cross-section through a coherent integrated two-layered web such as formed by the method and apparatus as illustrated by FIG. 1. A first layer 80 includes wood fibers entangled with nonparticle-containing meltblown fibers. A second layer 82 includes wood fibers entangled with particle-containing meltblown fibers. The particles 86 are also illustrated in FIG. 3. A formation line 85 of the first layer 80 and the second layer 82 is somewhat irregular as some of the meltblown fibers and wood fibers from each layer are intermingled.

Figure 4:
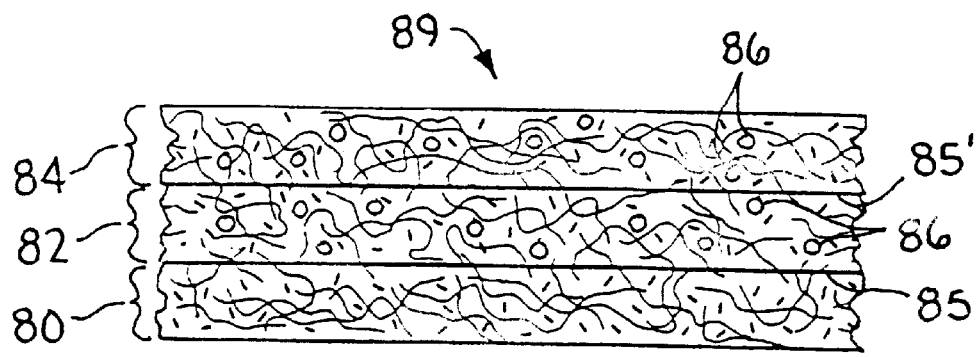
FIG. 4 illustrates a cross-section of a coherent integrated three-layered web of the present invention in which two layers of the web include particles.

FIG. 4 is illustrative of a cross-section through a coherent integrated threelayered web 89 such as may be formed by the method and apparatus of FIG. 2. As illustrated in the cross-section, a first layer 80 includes wood fibers entangled with nonparticle-containing meltblown fibers. A second layer 82 and a third layer 84 each include wood fibers entangled with particle-containing meltblown fibers. The particles 86 are also illustrated in FIG. 4. A formation line 85, between the first layer 80 and the second layer 82, is somewhat irregular as some of the meltblown fibers and wood fibers from the first and second layers are intermingled. Similarly, a formation line 85', between the second layer 82 and the third layer 84, is somewhat irregular as some of the meltblown fibers and wood fibers from the second and third layers are intermingled.

Figure 5:
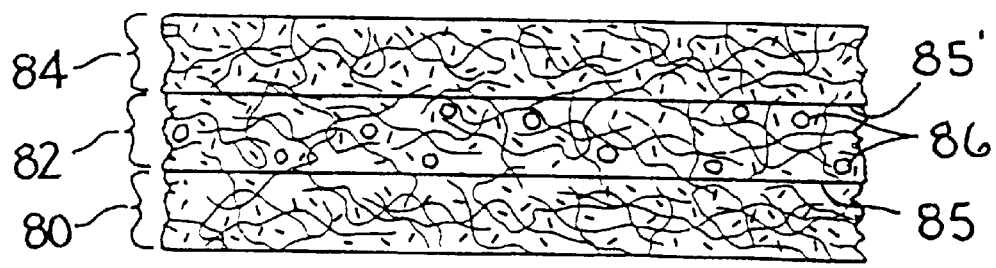
FIG. 5 illustrates a cross-section of a coherent integrated three-layered web of the present invention in which one layer of the web includes particles.

FIG. 5 illustrates an alternate embodiment of a meltblown web formed in accordance with the invention. In FIG. 5, a coherent integrated web having three layers is illustrated. A first layer 80 and a third layer 84 include wood fibers entangled with nonparticle-containing meltblown fibers. A second layer 82 includes wood fibers entangled with particle-containing meltblown fibers. The particles 86 are also illustrated in FIG. 5. A formation line 85, between the first layer 80 and the second layer 82, is somewhat irregular as some of the meltblown fibers and wood fibers from the first and second layers are intermingled. Similarly, a formation line 85', between the second layer 82 and the third layer 84, is somewhat irregular as some of the meltblown fibers and wood fibers from the second and third layers are intermingled. The structure of this web has the advantage that the particles are not exposed on either exterior surface of the web.

Figure 6:
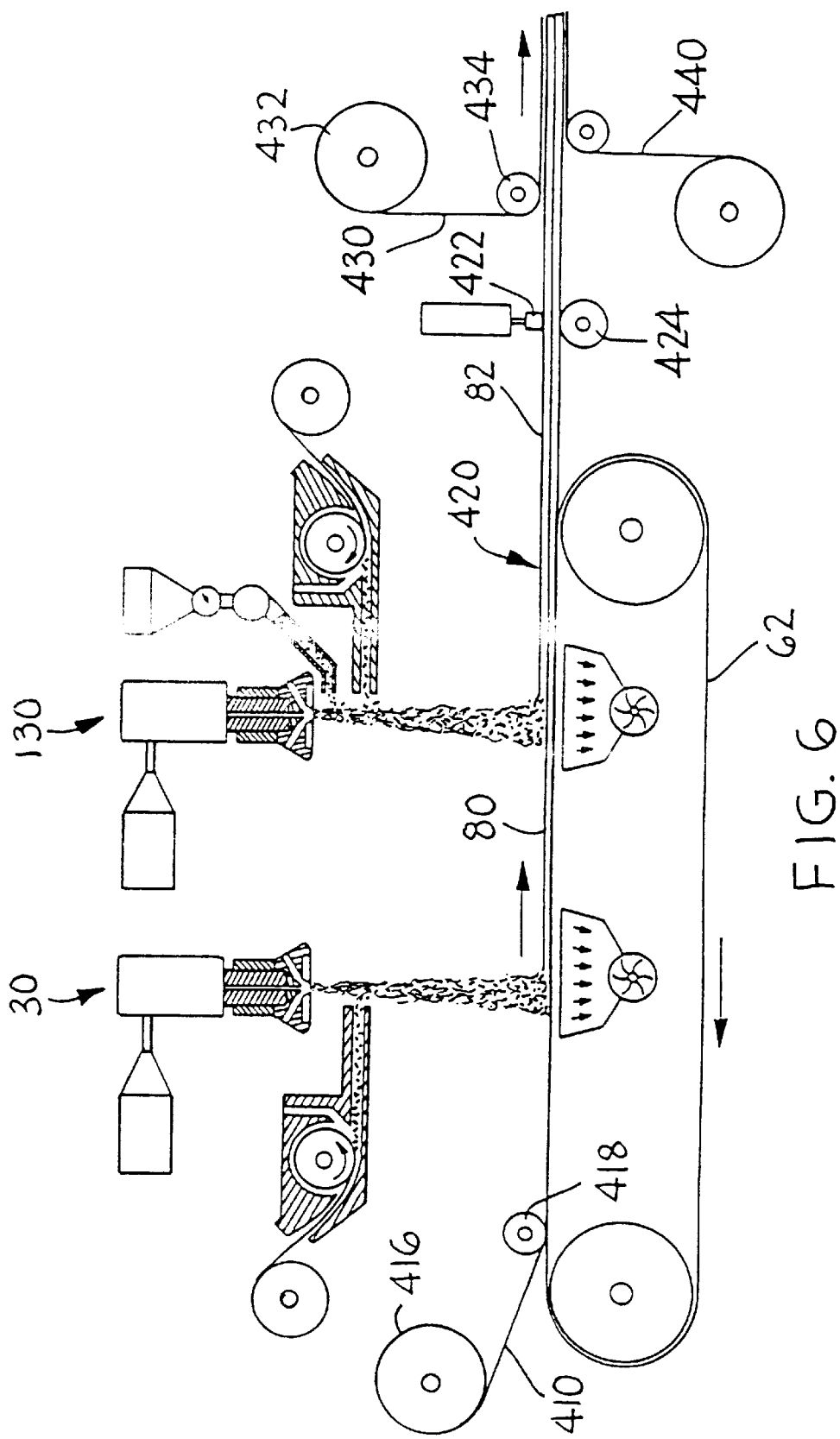
FIG. 6 illustrates an alternate embodiment of a forming apparatus in which the web is provided with embossing and combined with a carrier sheet.

FIG. 6 illustrates a forming apparatus such as previously illustrated in FIG. 1, but having some of the various optional peripheral devices that may be included with a forming apparatus in accordance with embodiments of the present invention. A base sheet 410 may be placed onto a moving forming surface 62 prior to application of a first layer 80 of a layered web 420. The base sheet 410 ordinarily would be a pervious sheet such as a spunbonded fabric sheet that would not interfere with gas flow through the moving forming surface 62. The pervious material would be applied from a roll 416 passing under an applicator roll 418 onto the moving forming surface 62. If it is desired to improve the strength of the layered web 420, it may be embossed either ultrasonically or at an elevated temperature so that the thermoplastic meltblown fibers are flattened into a film-like structure in the embossed areas. This film-like structure functions to hold the wood fibers more rigidly in place in the embossed areas. Thus, in the illustrative apparatus of FIG. 6, the layered web 420 is passed through an ultrasonic embossing station having an ultrasonic calendering head 422 vibrating against a patterned anvil roll 424. The embossing conditions (e.g., pressure, speed, power input) as well as the embossing pattern may be selected to provide the desired characteristics to the web. An intermittent pattern is desired with the area of the web occupied by the embossed areas, after passing through the embossing nip, being about 5 to about 50 percent of the surface area of the web, although the particular embossing conditions for any given material will depend on the composition of the material. It is also known to carry on embossing by the use of heated patterned embossing rolls. In addition to improving the strength of the web, the embossing process also improves the appearance of the web. It is further possible to apply a top sheet 430 to the layered web 420. The top sheet may be either a pervious sheet, an impervious layer, or another absorbent material. The top sheet 430 is applied from a roll 432 under an applicator roll 434. It also may be desirable to apply a carrier or bottom sheet 440 beneath the layered web 420. This carrier or bottom sheet may be particularly desirable if a forming sheet is not used as it will aid in handling of the web and then may be discarded. Thus, it can be readily appreciated that the present invention uniquely provides a variety of webs having one or more layers. It can also be readily appreciated that such webs could also have a single layer containing particles or include multiple layers having one or more layers containing particles in a variety of multi-layered configurations.

The composition of a layer having meltblown fibers and wood fibers, and the composition of a layer having meltblown fibers, wood fibers and particles may be varied over a wide range. The gas-forming of meltblown fibers and wood fibers in the manner described herein results in a web commonly called coform. This coform web may vary between about 10 percent meltblown fibers and about 90 percent wood fibers, and about 90 percent meltblown fibers and about 10 percent wood fibers. Generally, there is also a surfactant that is added to the web to aid in wetting of the polymer.

A wide variety of thermoplastic fiber-forming polymers are useful in forming the meltblown fibers, so that webs can be fashioned with different physical properties by the appropriate selection of polymers or combinations thereof. Among the many useful thermoplastic fiber-forming polymers, polyolefins such as polypropylene and polyethylene, polyamides, polyesters such as polyethylene terephthalate, and thermoplastic elastomers such as polyurethanes are anticipated to find the most widespread use in the preparation of the webs described herein.

The staple fiber blown into the coform may be any fiber that improves the absorbency or other property of the coform. Suitable staple fibers include polyester fibers, nylon fibers, cotton fibers and wood fibers. The preferred fiber is a wood fiber as the wood fibers formed from pulp are of desired size, low in cost and of high absorbency.

By "particle," "particles," "particulate," "particulates" and the like, it is meant that the particulate material is generally in the form of discrete units. The particles can comprise granules, pulverulents, powders or spheres. Thus, the particles may have any desired shape that would allow a portion of each heated particle to slightly penetrate into one or more solidifying meltblown fibers in accordance with the present invention. Desired particle shapes include, for example, cubic, rod-like, polyhedral, spherical or semi-spherical, rounded or semi-rounded, angular, irregular, etc. Shapes having a large greatest dimension/smallest dimension ratio, like, needles, fibers and flakes, are also contemplated for use herein. The desired shaped particles may be coated (gel-coated, protein coated and the like having a particulate core, a porous solid core, a solid core, a semi-solid core, a liquid core, a semi-liquid core, a gaseous core, a semi-gaseous core or combinations thereof) or uncoated (porous solid, solid, semi-solid and the like). It should be noted that more than one kind of particle may be used in some webs of the invention, either in mixture or in different layers. The use of "particle" and "particulate" may also describe an agglomeration comprising more than one particle, particulate or the like.

A wide variety of particles capable of slightly penetrating into one or more solidifying meltblown fibers in accordance with the present invention have utility in a three-dimensional arrangement in which they can interact with (for example, chemically or physically react with, or physically contact and modify or be modified by) a medium to which the particles are exposed. Included among the variety of particles having utility in the present invention are superabsorbents. The superabsorbent material suitable for incorporation in various embodiments of the present invention may be any superabsorbent that will maintain its particle integrity during the meltblowing process and exhibit good storage, handling, and resistance to gel-blocking properties. Typical of such superabsorbent materials are the water-insoluble hydrocolloidal particles derived from starches that will swell, but not dissolve when exposed to water. Also suitable for various embodiments of the invention are those superabsorbents formed from hydrolyzed cross-linked polyacrylamides, polyacrylates, polymers of acrylic polymers, or their copolymers. Such materials, when lightly cross-linked, are insoluble and, when dry, are solids that may be heated and blown in a gas stream, and maintain their integrity when impacting one or more solidifying meltblown fibers.

Also included within the scope and spirit of the present invention are particles suitable for use in controlling odor often emanating from absorbent articles used for absorption of body fluids such as menses, blood, urine, and other excrements. Suitable odor-controlling particles include activated charcoal or active carbon, baking soda, chitin, deodorizing materials such as clays, diatomaccous earth, zeolites, and complexes of potassium permanganate with active alumina, used alone or in combination.

Various embodiments of the present invention also contemplate including particles to control air-borne and vapor-borne odors, as well as including particulate material to slowly release a masking scent. The release of a masking scent can be achieved by using a superabsorber material that slowly releases an incorporated scent, similar to the mechanism by which superabsorbers slowly release moisture. As an example, time release fragrances, using a fragrance adsorbed on a particulate silica surface, can be incorporated in the meltblown web. Other deodorants and masking scents, also known in the art, which can be incorporated in particle form in the web, include the maladates, commonly known as chemical masking agents.

The amount of particles included in the meltblown web can depend on the particular use to be made of the web. In the present invention, particles may be added in any amount from a very minimum to an upper range which would be the amount that would stay in the web without causing the web to lose its integrity or the particles to undesirably drop out of the web during handling. The particles may be about 0.1 to about 80 percent, by weight, of the layer containing the particles. Generally, it is desired that the coform of any particular layer vary between about 90 weight percent wood fibers and about 50 weight percent wood fibers and between about 10 weight percent meltblown fibers and about 50 weight percent meltblown fibers for high absorbency and good handling properties.

In order to achieve a particular combination of properties in the web, there are a number of variables in both the primary and secondary streams that can be controlled along with the composition and basis weight of the web. Process parameters susceptible to control in a primary stream are the gas temperature, which is desirably in the range of about 600 to about 700° F. (about 315° C. to about 372° C.) within the ducts of the forming die; the gas volume, which is desirably in the range of about 250 to about 455 cubic feet per minute (about 118,000 to about 215,000 cubic centimeters per second) within the ducts of the forming die; the polymer extrusion rate, which is desirably in the range of about 0.25 grams per hole per minute; the polymer temperature; and the ratio of gas to polymer (mass flow rates) which is desirably in the range of about 10:1 to about 100:1. Variables that can be controlled in a secondary stream are the gas flow rate and the velocity of the picker roll; the gas velocity which is desirably in the range of about 3,000 to about 15,000 feet per minute (about 15 to about 76 meters per second); and the staple fiber size which is typically on the order of about 3 millimeters in length. Variables that can be controlled in a tertiary stream include the gas temperature which is typically in the range of about 130 to about 390° F. (about 54 to about 200° C.), and desirably about 150 to about 300° F. (about 65 to about 150° C.); the gas volume, which is desirably in the range of about 5 to about 20 cubic feet per minute (about 2,400 to about 95,000 cubic centimeters per second); and the particle size which is typically about 10 to about 350 microns in diameter. To minimize the likelihood of the meltblown fibers breaking upon impact of the particle, it is desired that the impact force (i.e., the velocity and mass of the particle) be no greater than the tensile strength (i.e., the maximum stress that a meltblown fiber can bear before it breaks or pulls apart, measured in force per unit of a cross-sectional area of the original meltblown fiber) of an individual meltblown fiber. If desired, additional streams of gas can be similarly adapted for use with the present invention.

The relationship between primary and secondary streams can also be controlled, and it is generally desired that the ratio of the gas velocities in primary and secondary streams be in the range of about 5:1 to about 10:1. The angle between primary and secondary streams at their point of merger may also be varied, but it is generally desired to have the two streams come together perpendicular to each other. Similarly, the particular point at which the two streams are merged, relative to the die tip of the forming die in the upstream direction and the moving forming surface in the downstream direction, may be varied.

The relationship between a primary stream and a tertiary stream can also be controlled, and it is generally desired that the ratio of the gas volumes in a primary stream and a tertiary stream be in the range of about 12:1 to about 90:1, depending, of course, on the size and mass of the particles. The angle between a primary stream and a tertiary stream at their point of merger may also be varied, but it is generally desired to have the two streams come together perpendicular to each other. Similarly, the particular point at which the two streams are merged, relative to the die tip of the forming die in the upstream direction and the moving forming surface in the downstream direction, may be varied.

A tertiary stream having heated particles can merge into a primary stream having meltblown fibers between the die tip of the forming die and the moving forming surface, provided that the heated particles can penetrate into the skin of one or more solidifying meltblown fibers upon impact. Thus, depending on the polymer, as well as the meltblowing method conditions, the point of merger typically is about 0 to about 2 inches (about 0 millimeters to about 51 millimeters) below the die tip. Desirably, the point of merger is about 0.5 to about 1 inch (about 13 to about 25 millimeters) below the die tip. To minimize the amount of residual heat lost by the particles to the environment upon exit from the feeder duct of a particle supply unit, it is desired that the particles travel a distance of about 0 to about 1 inch (about 0 to about 25 millimeters) upon exiting the feeder duct and merging with a primary stream. It is even more desired that the particles travel a distance of about 0 to about 0.5 inch (about 0 to about 13 millimeters) upon exiting the feeder duct and merging with a primary stream.

The invention has been described with the formation of coform webs. It is also within the invention to form successive layers of gas-formed meltblown webs, not containing wood fibers or other additional staple fibers, in which the first layer is without particles while the second or other successive layer does contain particles. In addition, it is also within the present invention to form a single layer gas-formed meltblown web, not containing wood fibers or other additional staple fibers, in which the single layer includes particles. For example, the forming apparatus as illustrated in FIG. 1 is capable of forming single-layer meltblown webs with particles if both the first meltblown unit 30 and the divellicating apparatus 152 of the second meltblown unit 130 are not operated. The phrases "meltblown layer" and "meltblown sheet", as used herein, mean a gas-formed meltblown layer of entangled meltblown fibers not containing staple fibers, whereas the term "coform" is a layer, as previously described, that contains staple fibers in addition to meltblown fibers. Typically the gas used in forming the gas-formed meltblown layers is air. Consequently, such a process is sometimes referred to as an air-forming or air-formed process which, in turn, typically produces one or more air-formed layers.

In an alternative embodiment, a layered web could be formed by the illustrated apparatus of the drawings of FIGS. 1, 2 and 6 by not operating the pulp sheet divellicating apparatus. In another alternative embodiment, a structure of one or more coform layers in coherent integral combination with one or more meltblown layers is also possible. Coform layers are desired over meltblown layers for most purposes as coform layers are higher in absorbency. The formation of various combinations of meltblown layers and coform layers is within the invention as is the placement of particles in either a meltblown layer or a coform layer.

A particle-containing web of the present invention finds uses in a variety of fields, depending, of course, on the particles employed. The web is particularly suitable for use in absorbent articles such as perineal shields and undergarments for the incontinent, bedpads, diapers, feminine hygiene products, and for body dressings such as those for wounds.

The novel method of the present invention renders the web substantially nondusting. As a result of rendering the web substantially nondusting, the web of the present invention advantageously may be economically die-cut into a variety of articles having predetermined shapes with substantially no particles undesirably dropping out of the sides of either the web or the die-cut article. The ability to die-cut the web enables the manufacturer to produce an absorbent article more efficiently and economically, resulting in lower production costs which could be passed on to the consumer. A further advantage of rendering the web substantially nondusting is that the die-cut absorbent articles need not be subjected to the additional step and expense of adding a peripheral seal to maintain the particles in the die-cut articles. In addition, certain embodiments of the web of the present invention have the advantage that the particles will not be presented to a body surface.

Figure 7:
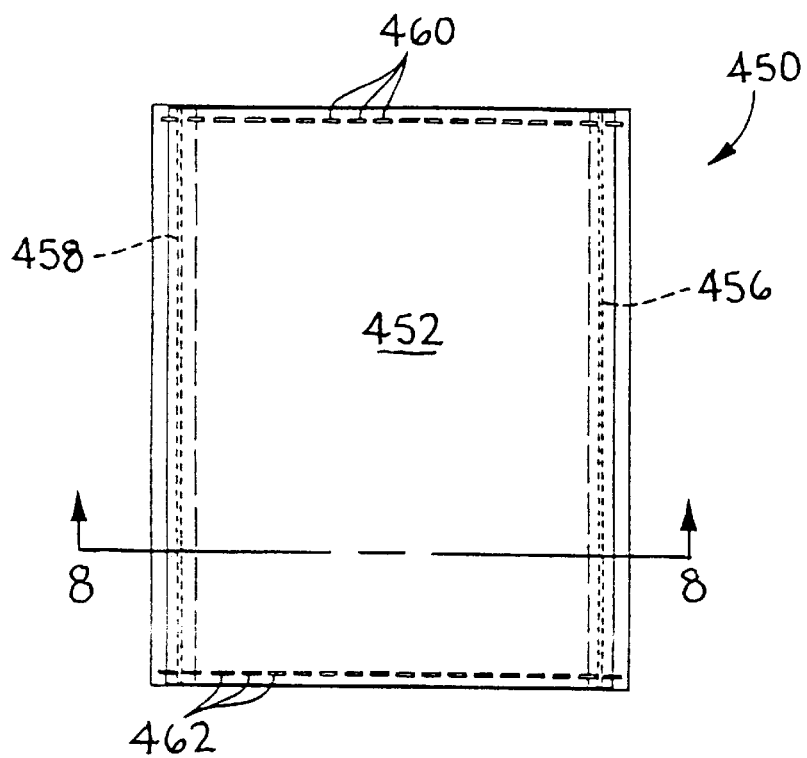
FIG. 7 illustrates a view of an absorbent article having a web of the invention.
Figure 8:
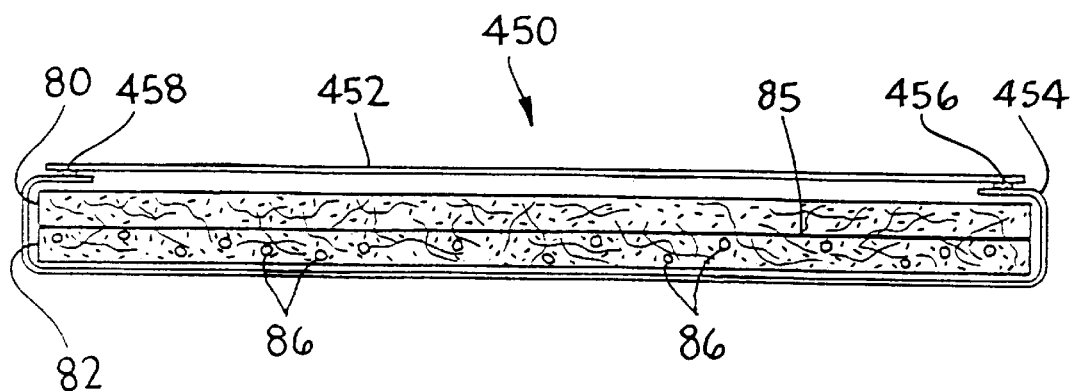
FIG. 8 illustrates a cross-section of the absorbent article of FIG. 7 taken along line 8—8 of FIG. 7.

As previously noted, depending on the type of particles incorporated therein, the web of the present invention has a variety of uses. For example, the material can be used in absorbent articles. FIGS. 7 and 8 depict one embodiment of such an absorbent article. The absorbent article 450 of FIGS. 7 and 8 is formed with the absorbent material of FIG. 3. The absorbent article 450 has an impervious polymer wrapping 454 and a body-side pervious member 452. The impervious wrapping is adhered to the pervious liner by glue lines at 456 and 458. The ends of the absorbent article may be ultrasonically sealed at 460 and 462. The coform material of layer 80 that does not have particulate material is exposed to the body of the wearer. The absorbent article 450 may be utilized for absorption of any body exudate. Depending on the type of particulate material used, typical uses of the absorbent article would include as incontinent devices, catamenial devices, diapers, or wound dressings.

Figure 9:
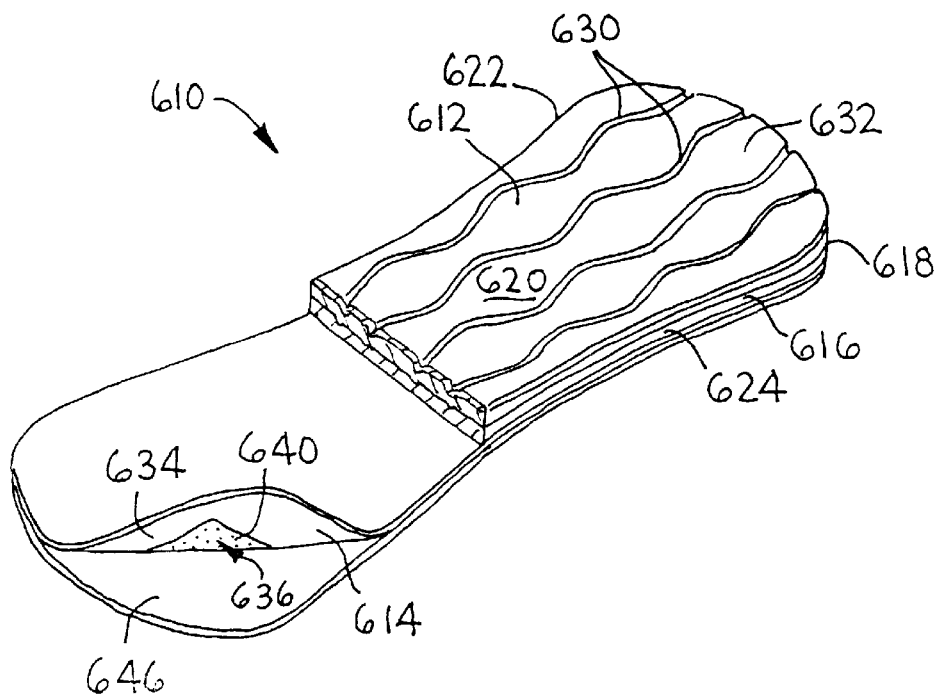
FIG. 9 illustrates a perspective partially broken-away view of an alternate absorbent article having a web of the invention.

Referring now to FIG. 9, another embodiment of an absorbent article is depicted. In FIG. 9, an absorbent article 610 is shown which is designed to be worn by a woman to absorb body fluids such as menses, blood, urine, and other excrements. The absorbent article 610 can be a sanitary napkin, a panty liner, a panty shield, an incontinent garment, or the like. A sanitary napkin is designed to absorb a greater quantity of fluid than a panty liner or panty shield. A sanitary napkin is usually longer, wider, and thicker than a panty liner and may contain a superabsorbent or other type of material, such as peat moss, which can increase its absorbent capacity. Sanitary napkins can have a length of about 6 to about 13 inches (about 152 to about 330 millimeters), a width of about 2 to about 5 inches (about 51 to about 127 millimeters), and a thickness of about 0.25 to about 25 millimeters. The sanitary napkin can have a variety of shapes including rectangular, hourglass, oval, or racetrack.

Panty liners, on the other hand, are relatively thin and small and can, but usually do not, contain a superabsorbent. A panty liner can have a length of about 5 to about 10 inches (about 127 to about 254 millimeters), a width of about 2 to about 3 inches (about 51 to about 76 millimeters), and a thickness of about 1.3 to about 3.6 millimeters.

Incontinent garments are usually equal to or larger than sanitary napkins. Incontinent garments can have a length of about 6 to about 33 inches (about 152 to about 838 millimeters), a width of about 2.5 to about 30 inches (about 64 to about 762 millimeters), and a thickness of about 19 to about 76 millimeters. Incontinent garments commonly have a rectangular or an hourglass shape.

The absorbent article 610 can include a liquid-permeable cover 612, a liquid-impermeable baffle 614, and an absorbent 616 positioned therebetween. The cover 612 can be formed of a nonwoven material, such as spunbond. The baffle 614 can be formed from a thin polyethylene film. The cover 612 and the baffle 614 can be eliminated, and the function of these two layers can be performed by other means. For example, the top surface of the absorbent 616 can serve as the cover, and an adhesive coating or a foam layer can replace the baffle.

The absorbent 616 has a body-facing surface and a garment-facing surface. The absorbent 616 can be a hydrophilic material formed from various types of natural or synthetic fibers including cellulose fibers, surfactant treated meltblown fibers, wood fibers, regenerated cellulose or cotton fibers, or a blend of pulp and other fibers. A desired absorbent material is the particle-containing coform material described herein and formed with the forming apparatus of FIG. 1. A coform mixture of about 70 percent wood fibers with about 30 percent polypropylene meltblown fibers generally works well.

The absorbent can also contain thermoplastic polymers which can be permanently deformed by the application of heat and pressure. Such materials include polypropylene, nylon, polyethylene, polyesters, etc. Typical of such materials are bonded carded webs, meltblown and spunbond fabrics.

The cover 612, baffle 614, and absorbent 616 are sandwiched together to form a pad 618. The pad 618 includes a central portion 620 with longitudinally-extending sides 622 and 624. The sides 622 and 624 can be either linear or non-linear so that the pad 618 can have various configurations. For example, the pad 618 can have a rectangular, a racetrack, an hourglass, or an oval-shaped configuration.

It should be noted that the pad 618 has a uniform thickness throughout. This enables the pad 618 to be die-cut during manufacture from a large sheet of laminated material. In addition, the pad 618 could optionally have tabs as disclosed in U.S. Pat. No. 5,429,630, issued Jul. 4, 1995, to Beal et al., which is incorporated herein by reference.

The pad 618 can contain a plurality of embossed areas 630. In FIG. 9, the embossed areas 630 are shown as sinusoidal lines formed parallel to the longitudinal axis of the absorbent article 610. The embossed areas can add integrity to the absorbent article 610 by securing the cover to the absorbent 616. The use of embossed lines gives an indication of ripples, or waves, which some consumers tend to associate with fluid absorption. The embossed areas 630 can be evenly spaced throughout the width of the absorbent article 610. The embossed areas 630 can also be in the form of dots, flowers, or the like.

The embossed lines 630 can be formed by running a laminate material through the nip of two rolls, the bottom roll being a pressure roll and the top roll being an embossing roll. The embossment will cause the cover 612 to be pinched down into the absorbent 616 and thereby assist the absorbent article 610 in being held together.

The pad 618 is formed out of a large sheet of laminate material which includes a cover 612, baffle 614, and absorbent 616. The pad 618 can be die-cut from this sheet of material and will have a body-facing surface 632 and a garment-facing surface 634. The body-facing surface 632 can be formed by the liquid-permeable cover 612, and the garment-facing surface 634 can be formed by the liquid-impermeable baffle 614.

Referring to FIG. 9, the absorbent article 610 further includes attachment means 636 secured to the garment-facing surface 634. The attachment means 636 can be a garment-attachment adhesive which provides a means for removably securing the pad 618 to the crotch portion of an undergarment, not shown. A garment attachment adhesive which works well is adhesive NS34-5516 which is commercially available from National Starch Company located at 10 Finderne Ave., Bridgewater, N.J. 08807. The attachment means 636 can include an adhesive 640 located on the central portion 620. The particular design and configuration of the attachment means 636 can vary.

Referring again to FIG. 9, the absorbent article 610 further includes at least one piece of release paper 646 covering the attachment means 636. The release paper 646 and the pad 618 can have coterminous exterior peripheries thereby facilitating a die-cut operation during manufacture. It is also possible to cut the release paper such that it covers all of the adhesive but has a configuration which lies within the outer periphery of at least a portion of the pad 618. For example, the release paper could run the length of the absorbent article 610, but be narrower than the overall width of the absorbent article 610. The release paper could also be cut larger than the pad 618, for example, having an outlying portion at one end so that the consumer could grasp the release paper and easily remove it from the pad 618.

The absorbent article 610 is designed to be die-cut from a sheet of laminate material including the cover 612, the baffle 614, the absorbent 616, the attachment means 636, and the release paper 646. The die-cutting operation enables the manufacturer to produce the absorbent article 610 efficiently and economically. Lower production costs could be passed on to the consumer.

Figure 10:
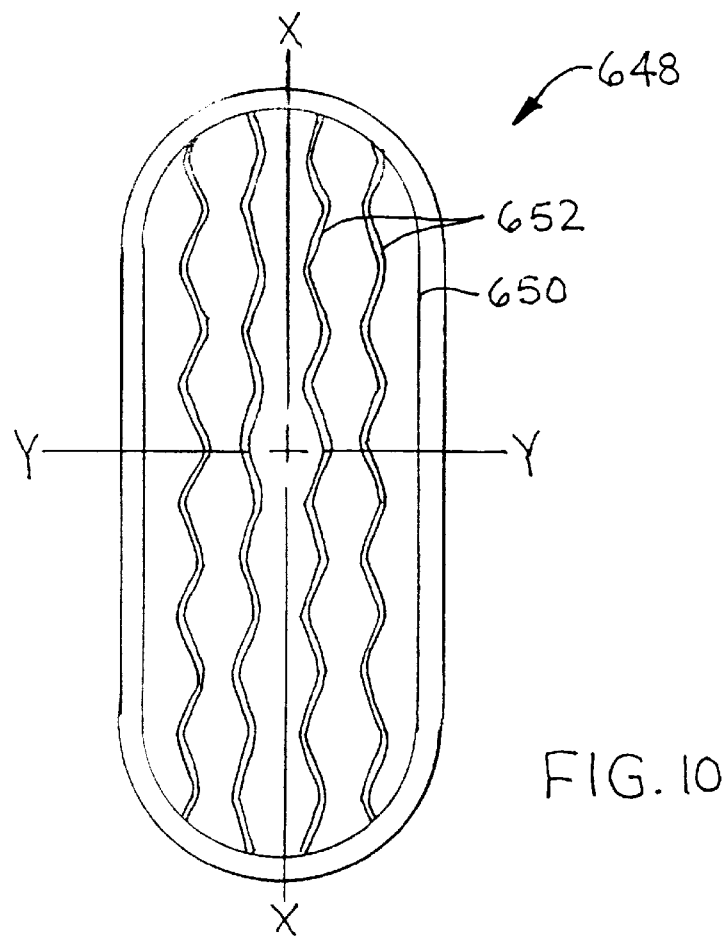
FIG. 10 illustrates a top view of an absorbent article having a web of the invention showing longitudinally-embossed lines and a continuous peripheral seal located inward from the periphery of the absorbent article.

Referring to FIG. 10, an absorbent article 648, such as a sanitary napkin or panty liner is shown. The absorbent article 648 is similar in construction to that discussed in FIG. 9, except that it includes a continuous embossed line 650 formed about 1/64 to about 1/2 inch (about 0.4 to about 13 millimeters) inward from the exterior periphery of the absorbent article 648. The embossed line 650 provides integrity between the cover and the absorbent and is advantageous in holding the article together when it is being removed from the crotch portion of an undergarment. The absorbent article 648 has a racetrack configuration with a longitudinal axis designated X—X and a transverse axis designated Y—Y. The absorbent article 648 also contains a plurality of sinusoidal embossed lines 652 which extend lengthwise across the absorbent article 648 with respect to the longitudinal axis X—X. The embossed lines 652 do not extend beyond the peripheral embossed line 650. When the absorbent article 648 is a sanitary napkin, it can have a surface area of less than about 30 square inches (about 194 square centimeters). Desirably, when the absorbent article 648 is a sanitary napkin, it has a surface area of less than about 25 square inches (about 161 square centimeters). When the absorbent article 648 is a panty liner, the surface area can be less than about 20 square inches (about 129 square centimeters).

When the absorbent article is a sanitary napkin, it can have a basis weight of less than about 400 grams per square meter, desirably less than about 300 grams per square meter, and most desirably less than about 250 grams per square meter. For a panty liner, the basis weight can be less than about 200 grams per square meter. Desirably, when the absorbent article is a panty liner, it has a basis weight of less than about 190 grams per square meter; more desirably, less than about 170 grams per square meter; and most desirably, less than about 150 grams per square meter. For a panty liner containing particulate material, the particulates can be incorporated in the meltblown web in amounts ranging from about 0.5 to about 30 grams per square meter, while the non-woven absorbent has a basis weight ranging from about 40 to about 350 grams per square meter.

EXAMPLES

The following Examples describe various embodiments of the invention. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the claims which follow the Examples. Parts, percentages and ratios are by weight unless otherwise indicated.

Example 1

Meltblowing Method Conditions:

Polymer Conditions:
  Polymer: PRO-FAX® Polypropylene (polypropylene homopolymer, homopolymer pellets), Grade PF-015, commercially available from Himont Incorporated, Hercules Plaza, Wilmington, Del. 19894, USA
  Temperature of Polymer at the Die Tip: approximately 510° F. (approximately 265° C.)
  Die Tip Pressure: approximately 86 psig
  Air Gap in the Ducts of the Forming Die: 18 to 20 thousandths of an inch
  Average Temperature of Air in the Ducts of the Forming Die: approximately 565° F. (approximately 296° C.)

Particle Conditions:
  Particles: 85% Baking Soda and 15% ABSCENTS® 5000(ABSCENTS® 5000 is an odor-controlling particle commercially available from UOP LLC, 25 East Algonquin Road, P.O. Box 5017, Des Plains, Ill. 60017, USA). The particles had a size range of about 5 to about 300 microns in diameter.
  Exit Temperature of Tertiary Stream: approximately 155° F. (approximately 68° C.)
  Gas Volume of Tertiary Stream: approximately 20 cubic feet per minute (approximately 95,000 cubic centimeters per second)

Pulp/Polymer Ratio: 70/30

Coform Only: 170 grams per square meter

The method described above resulted in the ABSCENTS® 5000 particles being incorporated in the meltblown web in a predetermined amount of about 2 to about 3 grams per square meter.

Example 2

Example 2 utilized the same Meltblowing Method Conditions as Example 1, except that the only particles present were ABSCENTS® 5000. The particles had a size range of about 20 to about 300 microns in diameter. The method described herein resulted in the particles being incorporated in the meltblown web in a predetermined amount of about 2 to about 3 grams per square meter.

Example 3

Example 3 utilized the same Meltblowing Method Conditions as Example 1, except that the only particles present were ABSCENTS® 3000, an odor-controlling particulate, commercially available from UOP LLC. The particles had a size range of about 5 to about 25 microns in diameter. The method described herein resulted in the particles being incorporated in the meltblown web in a predetermined amount of about 2 to about 3 grams per square meter.

Example 4

Meltblowing Method Conditions:
Polymer Conditions:
  Polymer: ESCORENE Polypropylene (granular resin), Grade PD 3505G, commercially available from Exxon Chemical Company, 13501 Katy Freeway, Houston, Tex. 77079-1398, USA
  Temperature of Polymer at the Die Tip: approximately 521° F. (approximately 272° C.)
  Die Tip Pressure: approximately 83 psig
  Air Gap in the Ducts of the Forming Die: 18 to 20 thousandths of an inch
  Average Temperature of Air in the Ducts of the Forming Die: approximately 570° F. (approximately 299° C.)
Particle Conditions:
  Particles: Baking Soda. The particles had a size range of about 5 to about 350 microns in diameter.
  Exit Temperature of Tertiary Stream: approximately 165° F. (approximately 74° C.)
  Gas Volume of Tertiary Stream: approximately 20 cubic feet per minute (approximately 95,000 cubic centimeters per second)
Pulp/Polymer Ratio: 70/30
Coform Only: 170 grams per square meter The method described above resulted in the particles being incorporated in the meltblown web in a predetermined amount of about 2 to about 3 grams per square meter.

Example 5

Example 5 utilized the same Meltblowing Method Conditions as Example 4, except that the only particles present were ABSCENTS® 5000. The particles had a size range of about 20 to about 300 microns in diameter. The method described herein resulted in the particles being incorporated in the meltblown web in a predetermined amount of about 2 to about 3 grams per square meter.

Example 6

Meltblowing Method Conditions:
Polymer Conditions:
  Polymer: Polypropylene (granules), Grade PD 3485, commercially available from Exxon Chemical Company
  Temperature of Polymer at the Die Tip: approximately 519° F. (approximately 271° C.)
  Die Tip Pressure: approximately 85 psig
  Air Gap in the Ducts of the Forming Die: 18 to 20 thousandths of an inch
  Average Temperature of Air in the Ducts of the Forming Die: approximately 571° F. (approximately 299° C.)
Particle Conditions:
  Particles: 85% Baking Soda and 15% ABSCENTS® 5000. The particles had a size range of about 5 to about 300 microns in diameter.
  Exit Temperature of Tertiary Stream: approximately 155° F. (approximately 68° C.)
  Gas Volume of Tertiary Stream: approximately 20 cubic feet per minute (approximately 95,000 cubic centimeters per second)
Pulp/Polymer Ratio: 70/30
Coform Only: 170 grams per square meter The method described above resulted in the ABSCENTS® 5000 particles being incorporated in the meltblown web in a predetermined amount of about 2 to about 3 grams per square meter.

Example 7

Example 7 utilized the same Meltblowing Method Conditions as Example 6, except that the only particles present were ABSCENTS® 5000. The particles had a size range of about 20 to about 300 microns in diameter. The method described herein resulted in the particles being incorporated in the meltblown web in a predetermined amount of about 2 to about 3 grams per square meter.

Example 8

Example 8 utilized the same Meltblowing Method Conditions as Example 6, except that the only particles present were ABSCENTS® 3000 from UOP LLC. The particles had a size range of about 5 to about 25 microns in diameter. The method described herein resulted in the particles being incorporated in the meltblown web in a predetermined amount of about 2 to about 3 grams per square meter.

In view of the foregoing, it will be seen that the several advantages of the invention are achieved and other advantageous results attained.

As various changes could be made in the above methods and meltblown webs without departing from the scope of the invention, it is intended that all matter contained in the foregoing description and shown in the accompanying drawings shall be interpreted as illustrative and not in a limiting sense.

I claim:
1. A method of forming a meltblown web, the method comprising:
   (a) forming at least one layer by the steps of:
      (i) forming a first primary stream containing meltblown fibers;
      (ii) forming a first secondary stream comprising staple fibers;
      (iii) merging the first primary stream and the first secondary stream so that the first primary stream comprises the staple fibers entangled with the meltblown fibers; and
      (iv) thereafter directing the first primary stream comprising the staple fibers entangled with the meltblown fibers onto a moving forming surface to form a first layer comprising the staple fibers entangled with the meltblown fibers;
   (b) forming at least one particle-containing layer by the steps of:
      (i) forming a second primary stream containing meltblown fibers;
      (ii) forming a first tertiary stream comprising heated particles;
      (iii) merging the second primary stream and the first tertiary stream so that the second primary stream comprises particle-containing meltblown fibers;
      (iv) forming a second secondary stream comprising staple fibers;

(v) merging the second primary stream comprising particle-containing meltblown fibers and the second secondary stream so that the second primary stream comprises the staple fibers entangled with the particle-containing meltblown fibers; and (vi) thereafter directing the second primary stream comprising the staple fibers entangled with the particle-containing meltblown fibers onto the first layer on the moving forming surface to form a second layer comprising the staple fibers entangled with the particle-containing meltblown fibers.

2. The method of claim 1, further comprising forming at least one additional layer by the steps of:

(a) forming a third primary stream containing meltblown fibers;

(b) forming a third secondary stream comprising staple fibers;

(c) merging the third primary stream and the third secondary stream so that the third primary stream comprises the staple fibers entangled with the meltblown fibers; and (d) thereafter directing the third primary stream comprising the staple fibers entangled with the meltblown fibers onto the second layer on the moving forming surface to form a third layer comprising the staple fibers entangled with the meltblown fibers.

3. The method of claim 1, further comprising forming at least one additional particle-containing layer by the steps of:

(a) forming a third primary stream containing meltblown fibers;

(b) forming a secondary tertiary stream containing heated particles;

(c) merging the third primary stream and the second tertiary stream so that the third primary stream comprises particle-containing meltblown fibers;

(d) forming a third secondary stream comprising staple fibers;

(e) merging the third primary stream comprising particle-containing meltblown fibers and the third secondary stream so that the third primary stream comprises the staple fibers entangled with the particle-containing meltblown fibers; and (f) thereafter directing the third primary stream comprising the staple fibers entangled with the particle-containing meltblown fibers onto the second layer on the moving forming surface to form a third layer comprising the staple fibers entangled with the particle-containing meltblown fibers.

4. The method of claim 1, wherein the particles are heat-stable particles.

5. The method of claim 4, wherein the particles have a temperature of about 50 to about 200° C.

6. The method of claim 4, wherein the particles have a temperature of about 65 to about 150° C.

7. The method of claim 3, wherein the particles are heat-stable particles.

8. The method of claim 7, wherein the particles have a temperature of about 50 to about 200° C.

9. The method of claim 7, wherein the particles have a temperature of about 65 to about 150° C.

10. The method according to claim 1, 2 or 3 wherein the staple fibers are wood fibers.

11. A method of forming a meltblown web, the method comprising forming at least one layer by the steps of:

(a) forming a primary stream containing meltblown fibers;

(b) forming a tertiary stream comprising heated particles;

(c) merging the primary stream and the tertiary stream so that the primary stream comprises particle-containing meltblown fibers;

(d) forming a secondary stream comprising staple fibers;

(e) merging the primary stream comprising particle-containing meltblown fibers and the secondary stream so that the primary stream comprises staple fibers entangled with the particle-containing meltblown fibers; and (f) thereafter directing the primary stream comprising the staple fibers entangled with the particle-containing meltblown fibers onto a moving forming surface to form a layer comprising the staple fibers entangled with the particle-containing meltblown fibers.

12. The method of claim 11, wherein the particles are heat-stable particles.

13. The method of claim 12, wherein the particles have a temperature of about 50 to about 200° C.

14. The method of claim 12, wherein the particles have a temperature of about 65 to about 150° C.

15. The method of claim 11, wherein the staple fibers are wood fibers.

* * * * *